US012797343B2

(12) United States Patent
Jetter

(10) Patent No.: US 12,797,343 B2
(45) Date of Patent: Nov. 17, 2026

(54) PATCH

(71) Applicant: APALOO GMBH, Talheim (DE)

(72) Inventor: Andreas Jetter, Tuningen (DE)

(73) Assignee: APALOO GMBH, Tuningen (DE)

( * ) Notice: Subject to any disclaimer, the term of this patent is extended or adjusted under 35 U.S.C. 154(b) by 469 days.

(21) Appl. No.: 18/258,297

(22) PCT Filed: Dec. 22, 2021

(86) PCT No.: PCT/IB2021/062207
§ 371 (c)(1),
(2) Date: Jun. 19, 2023

(87) PCT Pub. No.: WO2022/137177
PCT Pub. Date: Jun. 30, 2022

(65) Prior Publication Data

US 2024/0050380 A1 Feb. 15, 2024

(30) Foreign Application Priority Data

Dec. 22, 2020 (DE) ..................... 10 2020 134 781.2

(51) Int. Cl.
*A61K 41/00* (2020.01)
*A61K 9/70* (2006.01)
(Continued)

(52) U.S. Cl.
CPC ............ *A61K 9/7061* (2013.01); *A61K 41/00* (2013.01); *A61K 47/34* (2013.01); *A61K 47/38* (2013.01); *A61K 47/42* (2013.01)

(58) Field of Classification Search
None
See application file for complete search history.

(56) References Cited

U.S. PATENT DOCUMENTS 3,121,021 A 2/1964 Copeland
5,021,466 A * 6/1991 Cueli ........................ C08F 2/48
524/378

(Continued)

FOREIGN PATENT DOCUMENTS

DE 102014013448 A1 3/2016
WO 2011112643 A2 9/2011

OTHER PUBLICATIONS

Czech, ZR Pressure-sensitive acrylic adhesives (PSAs): how it began and the present state of art; ChemTexts 2024;10(6): 11 pages). (Year: 2024).*

(Continued)

*Primary Examiner* — Ernst V Arnold
(74) *Attorney, Agent, or Firm* — Biotech Beach Law PC; Raymond Wagenknecht

(57) ABSTRACT

A method of making a patch comprising the steps of (1) providing a carrier material; (2) coating an underside of the carrier material with a suitable non-UV-curable acrylic adhesive, the adhesive being a solution of a polyacrylate in an organic solvent or solvent mixture, the solvent or solvent mixture being used in an amount of from 25% to 70% by weight; (3) assembling the patch; (4) forming a grid structure on the patch so that it comprises a plurality of intersecting strips. According to the invention, the adhesive is applied at a temperature of 90° C. to 120° C. for a time of 5 s to 60 s, and before and/or after the application of the adhesive, the patch is activated by repeated irradiation of the underside by ultraviolet light.

13 Claims, 2 Drawing Sheets

(51) Int. Cl.

| | |
|---|---|
| *A61K 47/34* | (2017.01) |
| *A61K 47/38* | (2006.01) |
| *A61K 47/42* | (2017.01) |

(56) References Cited

U.S. PATENT DOCUMENTS

| | | | |
|---|---|---|---|
| 2005/0143544 | A1 | 6/2005 | Husemann et al. |
| 2014/0178599 | A1 | 6/2014 | Wright et al. |

OTHER PUBLICATIONS

PCT International Search Report for PCT/IB2021/062207 mailed Apr. 7, 2022.

Moskinto, "Moskinto Sliding Box", https://moskinto.de/products/mueckenpflaster, accessed Dec. 26, 2026.

Moskinto, Moskinto Mosquito Plasters, Itiching, Mosquitoes, Horse-flies, Bees, Mosquito Bites, Fly Bites, Sting Healers Against Iching, https://www.amazon.de/M%C3%BCckenpflaster-Schwellungen-Insektenstichen-Bienenstiche-Vespenstiche/dp/B075JP6K1M?th=1 , accessed Dec. 26, 2026.

Moskinto, "The plaster against itchy bites", Healthcare Professions—The Nursing Magazine (2018) 40(7-8):65.

* cited by examiner

PATCH

TECHNICAL FIELD

The invention relates to the field of medical technology. More specifically, the invention relates to a process for the production of an improved patch, and to a patch produced by this process.

STATE OF THE ART AND DISADVANTAGES

Quick wound dressings, also known as adhesive plasters, wound plasters or simply patches, are well known from the state of the art. They are used to cover small wounds. They protect them, for example, to reduce the risk of contamination by impurities entering the wound and/or to prevent the leakage of blood or wound fluid.

Such a patch comprises a carrier material, which is typically rectangular, round or oval. This is at least partially provided with an adhesive layer on the underside facing the wound. This layer has the task of releasably attaching the patch to the skin surrounding the wound.

In the case of a thermal plaster, for example, the entire underside can also be self-adhesive. In the central region of the underside, there is often a wound dressing that is not adhesive because it comes into contact with the actual wound.

Also known are such patches that accelerate the healing of the covered wound by keeping active substances ready in their wound pad. These are gradually released and absorbed by the tissue via the wound.

Active substances are also known which can be used to prevent the itching that occurs with insect bites. Accordingly, patches are known whose wound dressing contains an active substance that prevents or reduces itching.

A disadvantage of such patches is that their structure is more complex due to the multi-layered nature, and that the active ingredients are subject to a certain ageing process and/or can only be stored in a specific, narrow temperature range. Another disadvantage is the fact that such patches typically have to be sterilely packaged to prevent infection from a contaminated patch.

OBJECT OF THE INVENTION

Accordingly, the object of the invention is to provide a method for producing a patch and a patch produced by this method which avoids the disadvantages of the prior art.

According to this, the patch should have a simple structure and the effectiveness against itching caused by insect bites should be largely independent of the storage conditions and the storage time.

The problem is solved by a method for manufacturing a patch and a patch as described herein.

SUMMARY OF THE DISCLOSURE

First, a description of the method according to the invention for producing the improved patch is given. This is followed by a description of the patch produced by the process according to the invention.

The invention relates to a method of manufacturing a patch for reducing itching and/or swelling caused by insect bites. Such symptoms are particularly common side effects of such stings; although they are not normally dangerous, they are unpleasant and often require a relatively long time to subside. During their existence, the itching leads to corresponding scratching reactions of the affected person, which further delays the healing of the swelling.

The procedure comprises the following steps:

1) Providing an adhesive-coatable organic carrier material, preferably a carrier material comprising artificial silk, polyurethane or polyester. The carrier material ensures the physical integrity of the patch. It preferably has a thickness in the range of 0.1 to 1.0 mm, preferably it has a thickness of 0.25 mm. It is particularly preferably elastic, having a modulus of elasticity (Young's modulus) which is preferably between 0.05 and 5 gigapascals, and preferably between 0.5 and 2.0 gigapascals, at a temperature of about 20° C. to 40° C., and particularly preferably about 1.6 gigapascals at a temperature of 22° C.

2) Coating an underside of the carrier material with a non-UV-curing acrylate adhesive suitable for bonding the same to human skin, said adhesive being used as a solution of a polyacrylate in an organic solvent or solvent mixture, wherein the solvent or solvent mixture is used in an amount of from 25 to 70% by weight, preferably from 30 to 60% by weight, based on the total weight of the acrylate adhesive.

The solvent or solvent mixture is particularly preferably used in an amount of 40 to 55% by weight, based on the total weight of the acrylate adhesive.

The organic solvent or solvent mixture contained in the adhesive preferably contains at least one solvent selected from the group consisting of ethyl acetate, 2-propanol, heptane, toluene and 2,4-pentanedione. According to a further preferred embodiment, the solvent is selected from the group consisting of isopropanol, heptane and ethyl acrylate. Preferably, a solvent mixture is used which consists of at least 90% by weight of ethyl acetate, 2-propanol and/or heptane. If toluene and/or 2,4-pentanedione are used, their proportion in a solvent mixture is preferably not more than 10% by weight, the proportion of 2,4-pentanedione preferably being 0.3 to 5% by weight. Very particularly preferred is a solvent mixture comprising isopropanol, heptane and ethyl acetate. Even more preferred is a solvent mixture comprising isopropanol, heptane, ethyl acetate, toluene and 2,4-pentanedione. It is preferred that the solvent mixture comprises 30 to 35% by weight isopropanol, 30 to 35% by weight heptane, 30 to 35% by weight ethyl acetate, 3 to 9.5% by weight toluene and 0.5 to 2% by weight 2,4-pentanedione.

The acrylic polymer used according to the invention is preferably an acrylic copolymer, i.e. it is preferably composed of at least two different monomer units. Since it is used in solution, it is not a hot-melt adhesive. Except that the acrylic polymer is selected to be completely soluble in the organic solvent or solvent mixture, there is no further limitation. It has thus been shown that numerous acrylic polymers can be used according to the invention. The effect of the invention thus appears to be based on the combined effect of all the features set out in the independent claim.

The underside is the side that comes into contact with the skin during use. The adhesive has the task of permanently, but releasably, bonding the patch to the skin. "Permanent" in this context means a period of at least several hours up to several days. Preferably, the adhesive can be harmless with regard to even prolonged contact with the skin.

Advantageously, it should be possible to remove it from the skin together with the carrier material without leaving any residue and without exerting too much tensile force. Preferably, the underside of the carrier material is completely coated with the adhesive.

3) Tailoring the patch to a size suitable for covering a region from which the itch originates. In this context, "suitable" means that the size of the patch exceeds the typical size of a swelling caused by an insect bite by at least 0.5 cm, preferably by 1-2 cm. Accordingly, the size of the patch is at least 2×2 to 10×10 cm. The geometry can be, for example, rectangular, round or oval. "Tailoring" means to reduce or separate the patch, which typically comes from a larger sheet or a wider or at least longer roll, to the desired outer dimensions. This can be done by punching, mechanical cutting or laser cutting, for example.

4) Creating a grid structure on the patch so that it comprises a plurality of intersecting strips ("structuring"). A "grid structure" includes gaps that are created by the lack of material between said strips. The gaps are thus generated in the surface of the substrate (subtractive process) so that said grid structure is formed. This is characterised by regularly repeating gaps. It is clear that the excess material from the insertion of the gaps must also be removed from there and disposed of. The structuring can also be done by means of punching, mechanical cutting or laser cutting, for example.

Alternatively, the grid structure can also be formed by placing the strips next to and on top of each other in a suitable manner, spacing them accordingly (additive process).

The grid structure may also be formed by deploying a plurality of randomly intersecting strips, which may be linear or sinuous, and joining them together at the points of intersection; gaps are also formed in such a structure.

The grid structure leads to a reduction in the (global) E-modulus of the patch, as the amount of material available in the corresponding direction is smaller, reduced by the width of the gaps in the tensile direction.

According to the invention, the adhesive is applied to the carrier material at a temperature of 45° C. to 155° C. for a time of 5 s to 60 s. The adhesive is applied to the carrier material at a temperature of 45° C. to 155° C. Under these conditions, any solvent present in the adhesive is almost completely, preferably completely, evaporated. Preferably, the temperature is 90° C. to 120° C., and more preferably 105° C. The application time is preferably 10 s to 30 s, and particularly preferably 20 s. Tests have surprisingly shown that a patch in which the adhesive has been applied with the above parameters has particularly good properties with regard to effectiveness against itching and/or swelling, since the mechanical properties of the patch are thus influenced in a particularly advantageous manner.

According to the invention, the patch is also activated by repeated irradiation of the underside with ultraviolet light.

The irradiation is preferably carried out at a wavelength of 100 to 380 nm. The cumulative irradiation time is preferably 0.01 to 2 s, and is particularly preferably carried out by means of several, in particular 3 to 5, successive short light pulses. The time between the pulses is preferably such that the temperature of the irradiated surface falls back to the range of room temperature (21° C.+5° C.)

Preferably, UV-A light (wavelength 380 nm to 315 nm) is used first, followed by UV-B light (wavelength 315 nm to 280 nm) and/or UV-C light (wavelength 280 nm to 100 nm).

The irradiation takes place before or after the step of applying the adhesive. If the patch is irradiated before coating, the underside of the carrier material is prepared for the application of the adhesive, which in turn has a positive effect on the mechanical properties of the patch.

If irradiation takes place after the adhesive has been coated, the adhesive itself, and in particular its side intended for contact with the skin, is also modified in a beneficial way, which also has a positive effect on the mechanical properties of the patch, and in particular of the "composite system" of patch and skin.

Irradiation before as well as after the application of the adhesive is also possible in order to combine the advantages mentioned.

The irradiation also affects the stress pattern in the irradiated material. Irradiation with different wavelengths results in different penetration depths, which leads to different mechanical stress patterns at these depths.

As stated, it is preferred to combine the features "temperature" and "irradiation" described above. In this way, the mechanical properties of the patch, as well as the "composite system" of patch and skin, are optimally improved. The result is an increased effectiveness of the patch against itching and/or swelling once it has been applied to the affected area.

The addition of a known agent to reduce itching and/or swelling can be dispensed with. It has been shown that a patch produced by such a method is suitable for reducing itching and/or swelling caused by insect bites even without such an agent. In a preferred embodiment of the method, therefore, neither medicines nor active ingredients are added during the production of the patch. It has been shown that the positive effect of the patch is due in particular to the above measures. The patch according to the invention therefore preferably also contains neither medicines nor active ingredients.

The invention thus avoids the disadvantages known from the prior art. The construction of the patch according to the invention is very simple due to its possible and particularly preferred single-layer structure, which simplifies manufacture and reduces costs. Medical active ingredients can be completely dispensed with. Thus, the patch can be stored for up to 5 years before use. At the same time, it is significantly less sensitive to particularly high or low storage temperatures. At the same time, the manufacturing process according to the invention improves the mechanical properties of the patch, and thus also its effectiveness against itching and/or swelling.

Various embodiments of the invention are described in more detail below.

It should be noted that the tailoring step can be carried out before, after, and during the grid structure fabrication step. Tailoring with preceding or following production of the grid structure (subtractive or additive structuring) causes a shift of the stresses induced by the machining towards the centre of the patch or towards the edge of the patch. With simultaneous finishing and structuring, the stresses tend to be balanced over the entire patch. The stress state of the patch can also have an effect when it is attached to the skin.

Particularly preferably, the tailoring step takes place before or after, i.e. not simultaneously with, the structuring step, while the carrier material is at all times arranged with its underside coated with acrylate adhesive on a protective film. The mechanical processing associated with this is thus temporally two-stage. The protective film, which can be in the form of a release paper, ensures that it is easy to first structure (i.e. produce the gaps) and only then to tailor (i.e. separate the patches from each other), or vice versa.

Particularly preferably, between the two steps of "structuring" and "tailoring", a heat treatment of the product is carried out, at a temperature between 30° C. and 90° C., preferably of about 60°, and for a period of 2 to 120 seconds, preferably of 5 to 30 seconds, and particularly preferably of about 10 seconds. This treatment causes relaxation of the regions (edges) already treated by cutting or punching. In contrast, such treatment is not repeated after the subsequent further step, so that the stresses introduced by this further step continue to remain on the regions treated during this step. In this way, the patch has different internal stresses in its peripheral region (outer edges) than in its internal region (area of the gaps). Since the carrier material is placed on said protective film and remains there until it is used, this ensures that the stress state once created is maintained in the long term, since the carrier material cannot move or wrinkle, for example, to compensate for the stress gradient between the inner region and the edge. Since the patch is normally applied to the skin immediately after it is removed from the protective film, there is essentially no release of the internal tensions during this short period of time; rather, these are transferred to the user's skin, where they contribute to the desired effect of reducing itching.

Particularly preferably, the aforementioned activation is carried out by means of ultraviolet light by emitting a first pulse with a length of 5 s±1 s, followed by a first pause of 10 s±2 s, as well as a second pulse with a length of 5 s±1 s, followed by a second pause of 10 s±2 s, as well as a third pulse with a length of 2.5 s±0.5 s, onto the already applied adhesive layer. The dose irradiated onto the adhesive is preferably between 0.1 mJ/cm^2 and 1000 mJ/cm^2. It amounts particularly preferred to between 20 mJ/cm^2 and 200 mJ/cm^2. It is preferably 85 mJ/cm^2±15%. The repeated heating and cooling of the adhesive associated with this sequence achieves a particularly advantageous bond between the latter and the carrier material, and (later) between the adhesive and the skin. In addition, a particularly advantageous result of the above-mentioned activation is achieved.

The total irradiated dose should be between 0.1 mJ/cm^2 and 1000 mJ/cm^2. Preferably it is between 5 and 500 mJ/cm^2. Particularly preferably it is between 20 mJ/cm^2 and 200 mJ/cm^2. Preferably it is 85 mJ/cm^2±15%.

According to one embodiment, the grid structure consists of preferably three vertical strips and preferably four horizontal strips. Each strip is approximately 3 mm wide. The gaps between the strips have a width of 3 mm×3 mm. This results in a total width of 21 mm and a length of 27 mm.

Other preferred embodiments have dimensions of 36 mm×28 mm with a strip width of 4 mm, and also 4×3 strips, or of 52 mm×44 mm with 6×5 strips.

According to a further embodiment, the vertical strips and the horizontal strips are at an angle of 90° to each other. This means that a right-angled pattern results. The tool producing the gaps is accordingly placed (e.g. punching tool) or adjusted (e.g. cutting laser) so that the desired angles result. The gaps are then rectangular, such as square in particular. The advantage of this embodiment is a modulus of elasticity that is identical in both main tensile directions. (The main tensile directions are two tensile directions lying in the plane of the patch and perpendicular to each other). This is advantageous in cases where the patch is to be applied to an area of skin that stretches approximately equally in all directions, as the position of the patch then does not play a significant role.

According to an alternative embodiment, the vertical strips and the horizontal strips are at an angle of 7°, 30°, 42°, 45°, 60°, or 75° to each other. This results in gaps that have a rhombic shape. Depending on the angle, these rhombi are more or less flat. The advantage of this design is a modulus of elasticity that is different in the two main tensile directions. In cases where the patch is to be applied to skin areas with different elongation, this embodiment can be used to achieve a different mechanical reaction depending on the position on the skin.

According to a further embodiment, the grid structure consists of three or more groups of strips, each running parallel to the other. Each group encloses an angle to the remaining groups, so no group runs parallel to another group. The gaps then have—in the case of 3 groups—a triangular shape, in the case of 5 groups a pentagonal shape, and so on. Particularly preferred are 3 groups. The advantage of this embodiment lies in the provision of 3 directions with a higher modulus of elasticity and 3 further directions with a lower modulus of elasticity, which may be desirable in certain applications.

According to a preferred embodiment, each strip ends in a free section on both sides. "Both sides" means that the beginning and the end of the strip have a free section. The free sections lead to a non-linear edge of the patch. For example, while the envelope of the patch is rectangular, the actual contour is defined by the free sections. Alternatively, this structure can be created by placing the outermost gaps in such a way that their outer edge coincides with the outer edge of the envelope of the patch, or even by placing these gaps overlapping the outer edge. The advantage of such a design is the further improved interaction of the patch with the skin.

Preferably, the edges of each free section are at an angle of 90° to each other. Experiments have shown that edges shaped in this way achieve a particularly good working result. The corners of the sections cause a concentration of tension when the patch is applied to the skin, which further improves effectiveness.

According to an alternative embodiment, the ends of each free section taper at an angle of 10° to 170°. This means that the sections form "arrows" pointing away from the centre of the patch. The tips of these arrows also cause a concentration of tension when the patch is applied to the skin, further improving effectiveness.

According to another embodiment, the ends of each free section are rounded. In some cases, the concentration of stresses described above may be detrimental, which can be avoided by rounded ends.

According to another embodiment of the invention, the adhesive is dispensed at a pressure of from 1 bar to 10 bar, preferably from 2 bar to 6 bar, more preferably from 3.057 bar to 5.095 bar, and most preferably from 4.076 bar±0.05 bar. This means that the liquid or paste-like adhesive emerging from a dispensing device such as a nozzle does so at the aforementioned pressure. Alternatively, the pressure can be provided by application in an atmosphere having said pressure. Dispensing the adhesive under said pressure results in improved adhesion between the adhesive and the carrier material, which in turn has a beneficial effect on the mechanical properties of the patch.

According to a further embodiment, the adhesive is applied with a surface pressure of 200 kilopascals to 600 kilopascals, and preferably of 300 kilopascals to 500 kilopascals, and particularly preferably of 400 kilopascals, in each case±1%. This corresponds to a value of 2.03 kg/cm^2 to 6.1 kg/cm^2, preferably from 3.1 kg/cm^2 to 5.1 kg/cm^2, and particularly preferably 4.1 kg/cm^2. This surface pressure can be generated, for example, by means of a transfer plate after wetting the substrate and can be maintained for at least 0.5 seconds, preferably at least 2 seconds, and particularly preferably 3-5 seconds. In this way, a good bond between adhesive and carrier material is achieved.

According to a further preferred embodiment, the solvent is selected from the group consisting of isopropanol, heptane and ethyl acrylate.

The invention also relates to a patch for reducing itching and/or swelling caused by insect bites, the patch being manufactured by a method as described above. The advantages resulting from the shaping and treatment during manufacture are not repeated, instead reference is made to the preceding sections.

Particularly preferably, the carrier material of the patch comprises artificial silk, cellulose acetate, polyurethane or polyester. These materials are particularly skin-friendly, can be structured and treated well by means of the process according to the invention, and have the above-mentioned suitable modulus of elasticity in thicknesses of 0.1 and 1.0. Another advantage of cellulose acetate is its low moisture absorption capacity; thus, this material in fabric form tends to become electrostatically charged. While this effect is generally rather undesirable, it is preferable in the case of the present patch, as it thus attaches itself almost automatically to the skin. The effect is more pronounced with thinner and thus more flexible material thicknesses.

The weight percentage of the carrier material on the patch (without protective overlay) is preferably 50% to 70%, and of the adhesive 25% to 30%, more preferably 30% to 50%.

According to the invention, the adhesive is an acrylic adhesive (also: acrylate adhesive). Such an adhesive has proven to be particularly skin-friendly; moreover, it can be applied well at the temperatures and pressures provided for in the invention. Surprisingly, it has been shown that such an adhesive, although just not UV-curing, brings the advantages mentioned above through irradiation with UV light and in connection with the method according to the invention.

Preferably, the acrylic adhesive comprises as solvent for the polyacrylate the substances isopropanol, heptane and ethyl acetate.

An adhesive comprising these substances is particularly well suited to be bonded to the carrier material by means of the process according to the invention. In addition, an adhesive comprising these components has been found to be particularly skin-friendly and pleasant to remove again after the patch has been used.

BRIEF DESCRIPTION OF THE DRAWINGS

The invention is explained below by way of example with the aid of figures. Thereby shows FIG. 1 a schematic flow diagram relating to the process for producing an improved patch.

DETAILED DESCRIPTION

Figure 1:
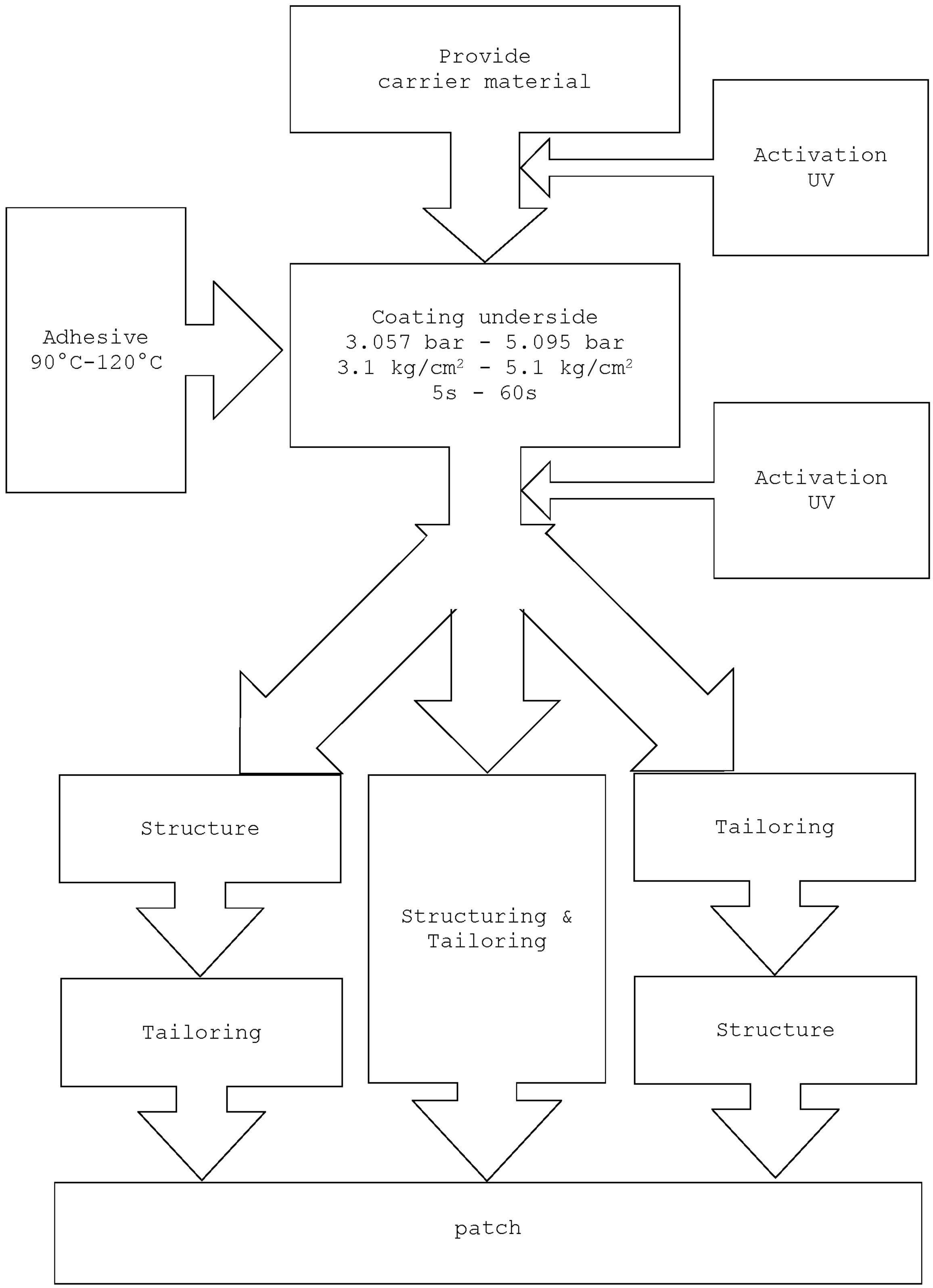

FIG. 1 shows a schematic flow diagram of the method for manufacturing an improved patch. In a first step, the carrier material is prepared. The adhesive is then applied to the underside of the carrier material, whereby the parameters mentioned in the figure with regard to temperature, time, pressure and surface pressure must preferably be adhered to. Then the structuring (production of the grid structure), as well as a finishing (separation of the patches from the panel) takes place. The last two steps can be carried out one after the other, as shown, but also at the same time.

According to the invention, the underside is activated by UV irradiation before and/or after coating.

To avoid repetition, reference is made to the above statements.

Figure 2:
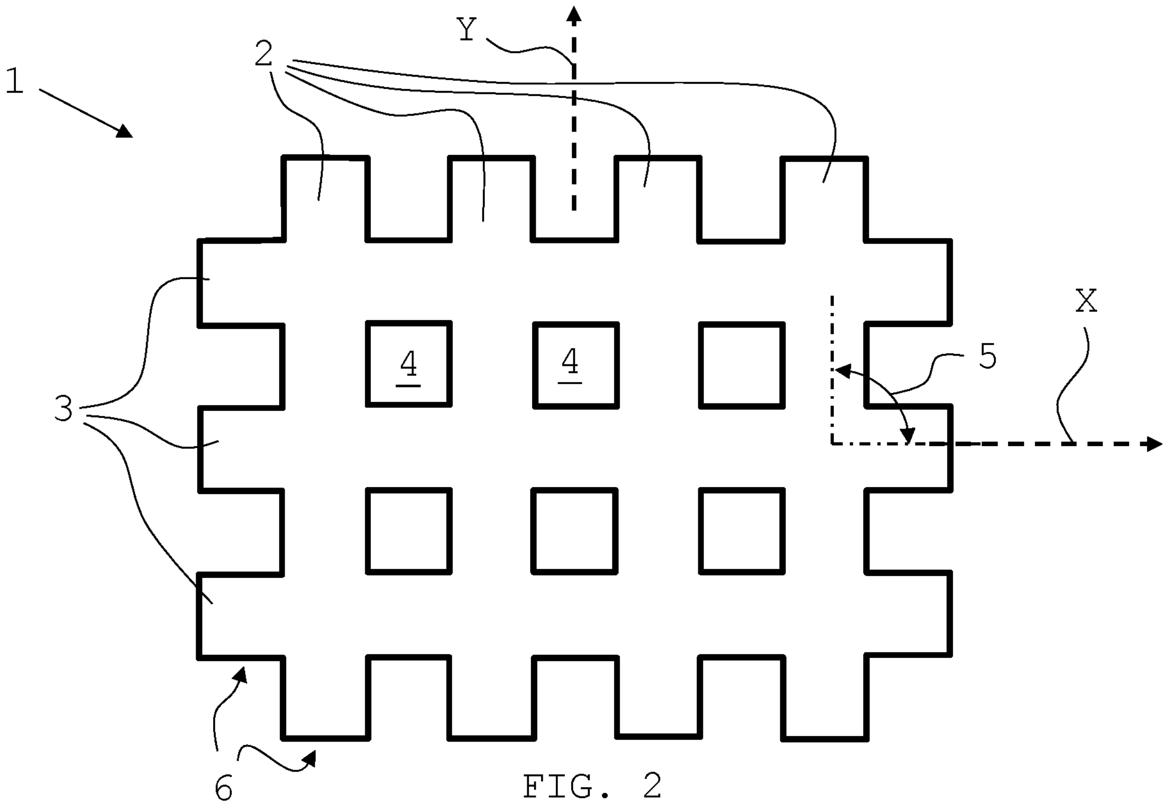
FIG. 2 a schematic representation of an embodiment of a patch according to the invention.

FIG. 2 shows a schematic representation of an embodiment of a patch 1 according to the invention. Accordingly, this patch 1 has a grid structure consisting of four vertical strips 2 and three horizontal strips 3. Between the strips 2, 3 there are gaps 4 (only two marked with a reference sign). The gaps 4 have the effect of reducing the elastic modulus of the patch (compared to an ordinary patch without gaps, not shown).

In the example shown, the vertical strips 2 and the horizontal strips 3 are at an angle 5 of 90° to each other. The gaps 4 are therefore rectangular, in this case square.

The embodiment shown in this Fig. has strips 2, 3 which end in free sections 6 on both sides (only two marked with reference signs). The edges of each free section 6 are at an angle of 90° to each other (no reference signs).

Figure 3:
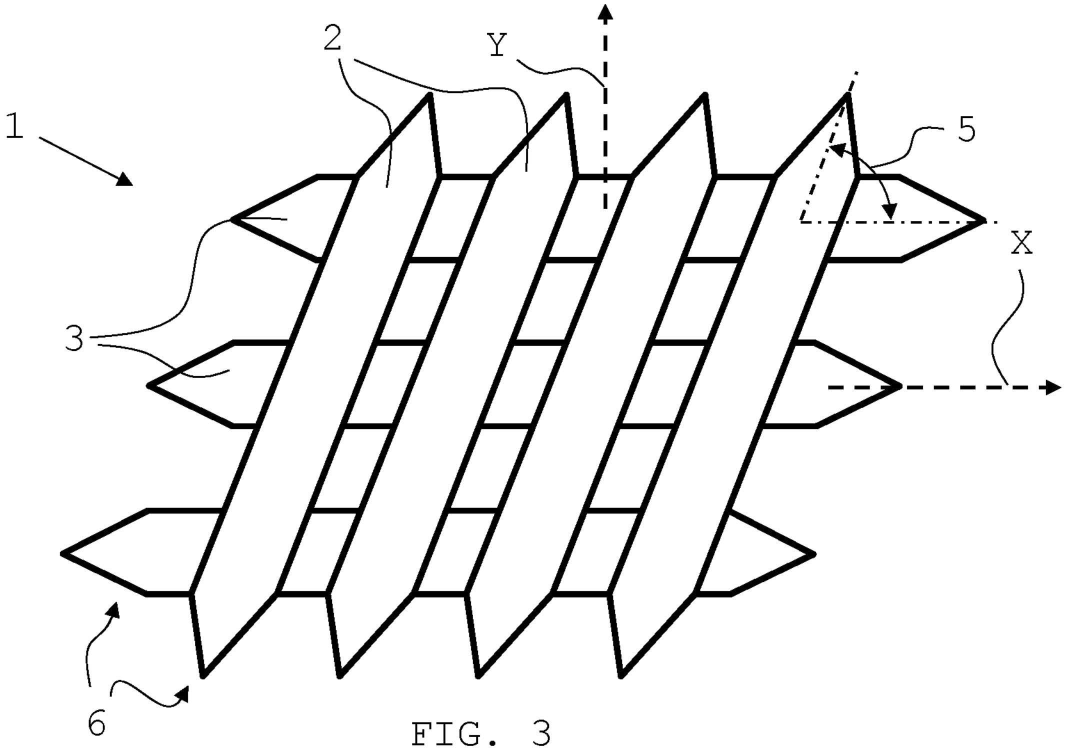
FIG. 3 a schematic representation of a further embodiment of a patch according to the invention.

FIG. 3 shows a schematic representation of another embodiment of a patch 1 according to the invention. This differs from the one described above in that the vertical strips 2 and the horizontal strips 3 are at an angle to each other that is different from 90°. In the present case, the angle 5 is approximately 68°. This results in different global moduli of elasticity for the two main tensile directions X, Y. In the main tensile direction Y, this is smaller than in the main tensile direction X. A load in the X-direction is mainly absorbed by the strips running in X-direction, which continue to be loaded along their longitudinal axis. When a load is applied in the Y-direction, however, the (tilted) vertical strips are no longer loaded in the direction of their longitudinal axis.

It also differs in that the gaps are not made in the substrate by punching or laser cutting, for example, but are formed by superimposing individual strips spaced apart from each other.

This embodiment also has strips 2, 3 which end in free sections 6 on both sides. However, the edges of each free section 6 taper at an angle of approximately 45°, which can lead to a concentration of tension at the tips after application of the patch 1 to the skin (not shown).

It should be noted that the variants described in FIGS. 2 and 3 are also possible in combinations other than those illustrated by the exemplary embodiments described, as they are not mutually dependent.

LIST OF REFERENCE SIGNS

1 Patch
2 Vertical strip
3 Horizontal strip
4 Gap
5 Angle
6 free section
X Main tensile direction
Y Main tensile direction

What is claimed is:

1. A method of manufacturing a patch for reducing itching and/or swelling caused by insect bites, the method comprising the following steps:

providing an adhesive-coatable organic carrier material, the carrier material comprising artificial silk, cellulose acetate, polyurethane or polyester;

coating an underside of the carrier material with a non-UV-curable acrylate adhesive suitable for bonding the patch to human skin, said adhesive being applied as a solution of a polyacrylate in an organic solvent or solvent mixture, wherein the solvent or solvent mixture is in an amount of 25 to 70% by weight, based on total weight of the acrylate adhesive, and the solvent is selected from the group consisting of isopropanol, heptane and ethyl acetate;

tailoring the patch to a size suitable for covering an area from which the itching and swelling originates;

producing a grid structure with gaps on the patch so that it comprises a plurality of intersecting strips;

wherein:

the adhesive is applied at a temperature of 45° C. to 155° C. for a time of 5 s to 60 s, and the patch is activated by repeated irradiation of the underside with ultraviolet light before and/or after application of the adhesive.

2. The method according to claim 1, wherein the step of tailoring takes place before or after the step of producing the grid structure, while the carrier material is at all times arranged with its underside which is coated with acrylate adhesive on a protective film.

3. The method according to claim 1, wherein the activation by means of ultraviolet light comprises a first pulse with a length of 5 s±1 s, followed by a first pause of 10 s±2 s, as well as a second pulse with a length of 5 s±1 s, followed by a second pause of 10 s±2 s, as well as a third pulse with a length of 2.5 s±0.5 s.

4. The method according to claim 1, wherein the energy radiated to the adhesive is 85 mJ/cm^2±15%.

5. The method according to claim 1, wherein the grid structure consists of vertical strips and horizontal strips.

6. The method according to claim 5, wherein the vertical strips and the horizontal strips are at an angle of 90° to each other.

7. The method according to claim 5, wherein the vertical strips and the horizontal strips are at an angle of 7°, 30°, 42°, 45°, 60°, or 75° to each other.

8. The method according to claim 1, wherein the grid structure consists of three or more groups of strips each running parallel to each other, and wherein each group includes an angle to the remaining groups.

9. The method according to claim 1, wherein each strip ends in a free section on both sides.

10. The method according to claim 9, wherein edges of each free section are at an angle of 90° to each other.

11. The method according to claim 9, wherein the ends of each free section are tapered at an angle of 10° to 170°.

12. The method according to claim 9, wherein the ends of each free section are rounded.

13. The method according to claim 1, characterized in that the adhesive is applied under a pressure of 3.057 bar to 5.095 bar or under a surface pressure of 3.1 kg/cm^2 to 5.1 kg/cm^2.

* * * * *